US00PP08723P

United States Patent [19]

Sato et al.

[11] Patent Number: Plant 8,723

[45] Date of Patent: May 10, 1994

[54] VARIETY OF LIMONIUM NAMED OCEAN BLUE

[75] Inventors: Kazunori Sato; Kazuharu Koreeda, both of Shizuoka; Nobuaki Takanashi, Kanagawa, all of Japan

[73] Assignee: Dai-Ichi Engei Plantech Co., Ltd., Tokyo, Japan

[21] Appl. No.: 72,716

[22] Filed: Jun. 7, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Webb, Burden, Ziesenheim & Webb

[57] ABSTRACT

A new variety of Limonium is tall with upright stems. The flower color is a bluish-purple. The flowers are long-lasting and the plant is easy to grow. Up to 8 stems flowers can be cut in the first year and 10–12 flower stems in the second year.

1 Drawing Sheet

BACKGROUND OF THE INVENTION

The present invention comprises a new and distinct cultivar of the genus Limonium known by the varietal name 'Ocean Blue' (registered name in Japan is 'Diacean'). The new variety was discovered in a selected breeding program by Messrs. Kazunori Sato, Kazuharu Koreeda and Nobuaki Takanashi. The new variety is an interspecific hybridization between two limonium species. The seed parent was Limonium latifolia (LA-11) and the pollen parent were numbered plants of Limonium caspia. The new variety is similar in color to both the seed and pollen parent and is ever-flowering in a manner similar to the seed parent. The new variety differs from the parentage in that the stem is longer than the seed parent and harder than the pollen parent.

The new cultivar was discovered in 1988 at the Dai-Ichi Engei Plantech Co., Ltd., 1101-8, Ueno, Oyama, Sunto, Shizuoka, Japan. The new cultivar was first asexually reproduced by cuttings at Dai-Ichi Engei Plantech Co., Ltd. and has been repeatedly asexually reproduced by cuttings at the same location. It has been found to retain its distinctive characteristics through successive propagation. The climate where the new variety was discovered is generally considered to be cool climate.

DESCRIPTION OF THE DRAWING

The accompanying colored photograph illustrates the new cultivar, the color being as true as possible with color illustrations of this type.

DESCRIPTION OF THE NEW PLANT

The following detailed description sets forth the characteristics of the new cultivar. The data which defines these characteristics were collected from asexual reproductions grown in a greenhouse under wintertime temperature of 53°–68° F. and summertime temperature of 68°–86° F. The plant histories were taken of plants blossomed under full light in a greenhouse and the color readings were taken under sunlight. Color references are primarily to the R.H.S. Colour Chart of The Royal Horticultural Society of London.

THE PLANT

Classification:

*Botanical.*—Limonium.

*Commercial.*—Limonium (statice) hybrid.

Form: Straight.

Growth: Medium.

Branching: Many. Many definite spikes.

Height from soil line: 45 inches.

Spread: 30 inches.

Hardiness: Can tolerate range of 10° to 95° F.

Disease resistance: No known disease problem.

Effects of weather: When planted outdoors, the plants tend to be shorter than in a greenhouse.

Cutting: Up to 8 flowers can be cut in the first year and 10 to 12 in the second year.

THE BUD

Size: 0.13 inches in diameter.

Rate of opening: Greater than 80%.

Petals: Medium.

Color: Violet Group 86C.

INFLORESCENCE

Fully expanded: 30 inches.

Stems: 45 inches.

Form: Panicle.

Permanence: Long lasting.

Color:

*Tonality from a distance.*—Bluish-purple.

*Front of petals.*—Violet group 82C.

*Reverse of petals.*—Violet group 82C.

*Base of petals.*—Yellow-green group 155D.

*Throat.*—Green group 138B.

*Discoloration.*—Does not fade.

Petals:

*Texture.*—Thin.

*Appearances.*—Five pieces, polypetal, all petals have the same shape.

*Arrangement.*—Radial.

*Persistence.*—Good.

*Fragrance.*—Mild.

REPRODUCTIVE ORGANS

Anthers: 0.01 inch, Green-yellow group 2C.

Stamen: 0.26 inches.

Filament: 0.24 inches and White Group 155D.

Ovaries: 0.06 inches and Yellow-green group 145C.

Pollen: Not detectable.

Stigma: Extremely small and thin when present and generally not detectable.

Pistils: 0.28 inches.

Foliage:

*Size.*—10 inches.

*Quantity.*—25-30.

*Shape.*—Egg-like shape.

*Rib and vein color.*—Green group 144C.

*Margin.*—Smooth and flat.

We claim:

1. A new and distinct variety of Limonium as shown and described herein and characterized by its bluish-purple color, height, and upright stems.

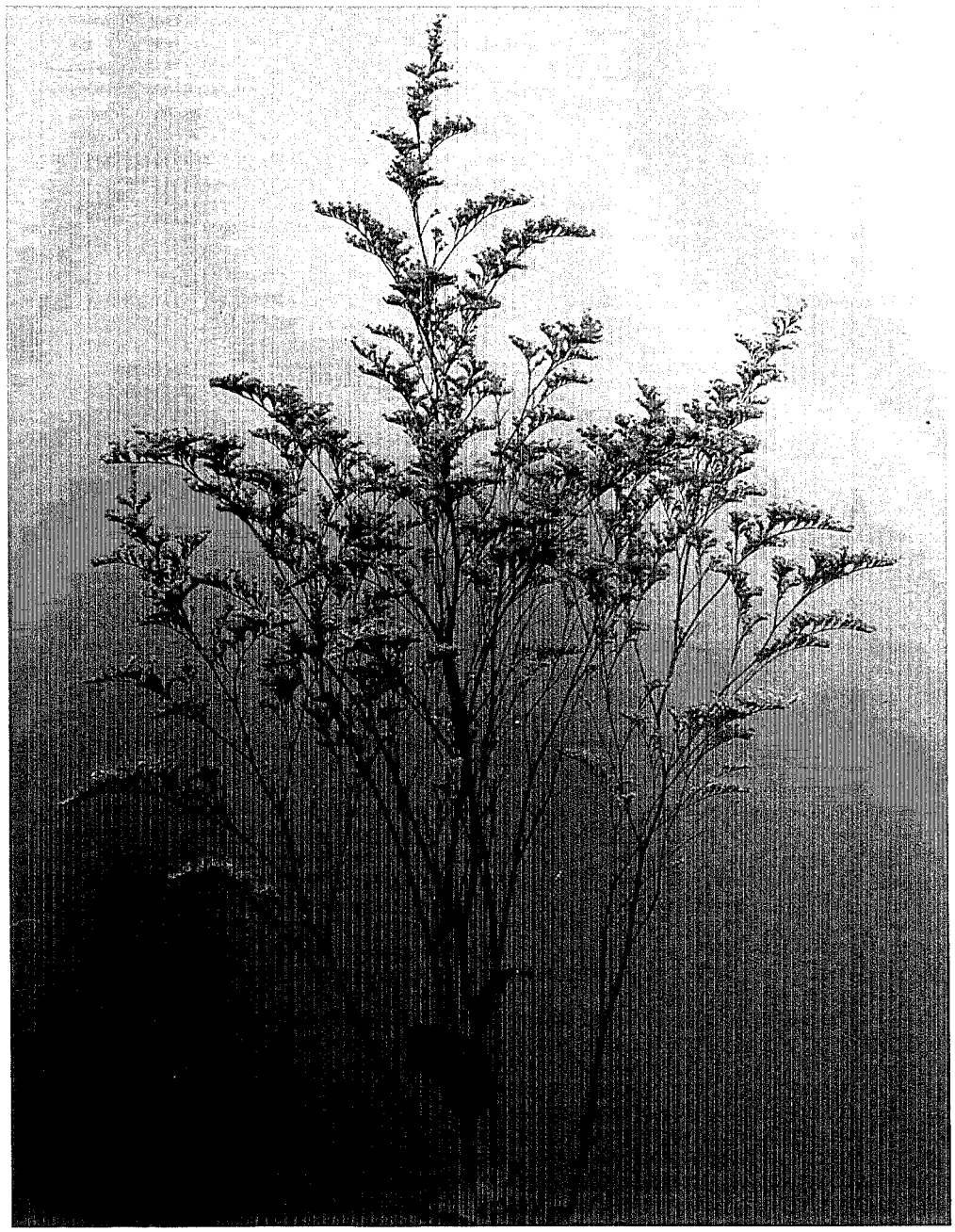

* * * * *